(12) United States Patent
Eom et al.

(10) Patent No.: US 9,487,461 B2
(45) Date of Patent: Nov. 8, 2016

(54) METHOD FOR PREPARING METHYLOL ALKANAL

(71) Applicant: LG CHEM, LTD., Seoul (KR)

(72) Inventors: Sung Shik Eom, Daejeon (KR); Min Soo Kim, Daejeon (KR); Tae Yun Kim, Daejeon (KR); Dong Hyun Ko, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/441,765

(22) PCT Filed: Jul. 21, 2014

(86) PCT No.: PCT/KR2014/006606
§ 371 (c)(1),
(2) Date: May 8, 2015

(87) PCT Pub. No.: WO2015/012550
PCT Pub. Date: Jan. 29, 2015

(65) Prior Publication Data
US 2015/0291496 A1    Oct. 15, 2015

(30) Foreign Application Priority Data

Jul. 26, 2013  (KR) .................. 10-2013-0088775
Jul. 14, 2014  (KR) .................. 10-2014-0088469

(51) Int. Cl.
*C07C 45/00*    (2006.01)
*C07C 45/75*    (2006.01)
*C07C 45/86*    (2006.01)

(52) U.S. Cl.
CPC ............... *C07C 45/75* (2013.01); *C07C 45/86* (2013.01)

(58) Field of Classification Search
CPC ....................................... C07C 45/75
USPC .......................................... 568/464
See application file for complete search history.

(56) References Cited

U.S. PATENT DOCUMENTS 5,994,592 A * 11/1999 Yokoyama ............ C07C 45/75
562/523

FOREIGN PATENT DOCUMENTS

| JP | 51-005367 A | 1/1976 |
|---|---|---|
| KR | 10-2000-0062250 A | 10/2000 |
| KR | 10-2005-0114274 A | 12/2005 |
| KR | 10-2011-0098941 A | 9/2011 |
| KR | 10-2011-0110303 A | 10/2011 |
| WO | 2004/092097 A1 | 10/2004 |

* cited by examiner

*Primary Examiner* — Porfirio Nazario Gonzalez
*Assistant Examiner* — Kofi Adzamli
(74) *Attorney, Agent, or Firm* — Dentons US LLP

(57) ABSTRACT

Disclosed is a method of preparing methylol alkanal. According to the present invention, a yield of methylol alkanal may be improved without using formaldehyde in an excess amount of a theoretical minimum molar ratio or more, formaldehyde wastewater may be reduced, and the amount of formaldehyde remainder, which may act as a hydrogenation catalyst poison, comprised in the methylol alkanal is decreased when the prepared methylol alkanal is hydrogenated resulting in improvement in efficiency of the hydrogenation.

15 Claims, 1 Drawing Sheet

METHOD FOR PREPARING METHYLOL ALKANAL

This application is a National Stage Entry of International Application No. PCT/KR2014/006606, filed on Jul. 21, 2014, and claims the benefit of Korean Application No. 10-2013-0088775, filed on Jul. 26, 2013 and Korean Application No. 10-2014-0088469, filed on Jul. 14, 2014, all of which are hereby incorporated herein by reference in their entirety.

TECHNICAL FIELD

The present invention relates to a method of preparing methylol alkanal. More particularly, the present invention relates to a method of preparing methylol alkanal to reduce formaldehyde wastewater by reducing an amount of formaldehyde remaining in methylol alkanal and, at the same time, increase a yield of methylol alkanal.

BACKGROUND ART

Trimethylolalkanes are useful as a raw material of alkyd resins, polyurethane resins, (un)saturated polyester resins, synthetic lubricants, surfactants, reactive monomers, and the like.

Trimethylolalkanes may be prepared through hydrogenation of dimethylolalkanes (hereinafter, called methylol alkanal). A process of preparing methylol alkanal by reacting formaldehyde and alkyl aldehyde in the presence of an amine based catalyst is generally performed in one batch type process (See FIG. 2).

A yield of methylol alkanal is determined by a molar ratio of added formaldehyde and alkyl aldehyde. To increase selectivity of methylol alkanal, formaldehyde is used in an excess amount of a theoretical minimum molar ratio or more.

However, formaldehyde used as a raw material is used as an aqueous solution having a purity of approximately 30% to 42% due to properties thereof. Therefore, the amount of wastewater after reaction increases as much as the amount of formaldehyde used in an excess amount. In addition, since it is difficult to isolate entire formaldehyde included in methylol alkanal, an amount of formaldehyde remaining in methylol alkanal may function as a catalyst poison in hydrogenation when methylol alkanal is hydrogenated.

DISCLOSURE

Technical Problem

Therefore, the present invention has been made in view of the above problems, and it is one object of the present invention to provide a method of preparing methylol alkanal, which may improve a yield of methylol alkanal without using formaldehyde in an excess amount of a theoretical minimum molar ratio or more.

It is another object of the present invention to provide a method of preparing methylol alkanal to reduce the amount of formaldehyde remaining in methylol alkanal and, at the same time, increase the amount of methylol alkanal of a reaction product.

Technical Solution

In accordance with one aspect of the present invention, provided is a method of preparing methylol alkanal comprising 0.5 to 5 wt % of a formaldehyde remainder of a reaction product by reacting formaldehyde and alkyl aldehyde in the presence of an amine based catalyst.

Hereinafter, the present invention will be described in more detail.

Alkyl aldehyde used in the present invention may be, for example, a normal type and isotype having a C4 to C5 alkyl group. As a specific embodiment, the alkyl aldehyde may be normal butylaldehyde.

In addition, the amine based catalyst used as a reaction catalyst of the alkyl aldehyde and formaldehyde may be, for example, a conventional weak base catalyst such as a tertiary amine, and the weak base catalyst may be used in a conventional catalytic amount.

As a specific embodiment, the tertiary amine may be selected from triethylamine, trimethylamine, dimethyl ethylamine, cyclohexyl dimethylamine, methyl diethyl amine, and a mixture thereof.

In addition, as one embodiment, the methylol alkanal may be dimethylol butanal, hydroxy pivalaldehyde, or a mixture thereof.

In particular, when formaldehyde and alkyl aldehyde are reacted in the presence of an amine based catalyst, a conversion rate of added formaldehyde increases and, thus, methylol alkanal comprising 0.5 to 5 wt % or 0.7 to 3.9 wt % of formaldehyde remainder is prepared.

A reaction molar ratio of the formaldehyde to the alkyl aldehyde may be 2 or less. In one embodiment, when dimethylol butanal as a methylol alkanal is prepared using normal butylaldehyde as an alkyl aldehyde, 2 mol of formaldehyde and 1 mol of normal butylaldehyde are theoretically required to prepare dimethylol butanal. However, to increase selectivity of dimethylol butanal, formaldehyde is used in an excess amount of 2 mol or more.

Meanwhile, the amount of formaldehyde initially added in the present invention may be 20 to 70 wt % with respect to 100 wt % of the total amount of alkyl aldehyde divisionally added per step.

That is, the present invention is characterized in that a reaction molar ratio of formaldehyde to alkyl aldehyde is 2 or less, or 0.5 to 1.63 while using formaldehyde in a minimum amount of 20 to 70 wt % with respect to 100 wt % of the total amount of alkyl aldehyde.

In the methylol alkanal prepared according to the present invention, a ratio of the amount of methylol alkanal (%) to the amount of formaldehyde remainder (%) of the reaction product may be 10 or more or 10 to 40.

In addition, in the methylol alkanal prepared according to the present invention, a ratio of the amount of methylol alkanal (%) to the formaldehyde conversion rate (%) calculated from an amount of the formaldehyde remainder of the reaction product may be 0.25 or more, 0.25 to 0.525, or 0.281 to 0.525.

In one embodiment, the preparation process of the present invention described above may be carried out using a continuous reaction device in which the reactor for improving selectivity of the methylol alkanal and the reactor for reducing the amount of formaldehyde remaining in the methylol alkanal are connected in series as illustrated in FIG. 1.

So long as not differently specified, the expression "reactor for improving selectivity of methylol alkanal" means a first reactor of the continuous reaction device constituted of a total of n reactors and the expression "reactor for reducing the amount of formaldehyde remainder" means all of the other reactors, except for the first reactor, of the continuous reaction device constituted of a total of n reactors.

As a specific embodiment, n may be 2 to 4. When n is 4 (that is, a total of 4 reactors are continuously equipped), a first equipped reactor corresponds to the reactor for improving selectivity of methylol alkanal, and all of a second, third, and fourth reactor, and the like correspond to the reactor for reducing the amount of formaldehyde remainder.

That is, alkyl aldehyde may be divisionally added to each of the reactor for improving selectivity of methylol alkanal and the reactor for reducing the amount of formaldehyde remainder.

In one embodiment, the alkyl aldehyde may be equally and divisionally added. In addition, a divisional addition amount thereof may be controlled depending on a yield of methylol alkanal required.

Meanwhile, formaldehyde and tertiary amine may be added batchwise to the reactor for improving selectivity of methylol alkanal. In this regard, as described above, the addition amount of formaldehyde may be controlled to 20 to 70 wt % with respect to 100 wt % of the total amount of alkyl aldehyde divisionally added.

The reactor for reducing the amount of formaldehyde remainder may be constituted of 1 to 3 reactors. The reactor for reducing the amount of formaldehyde remainder is preferably connected in series with the reactor for improving selectivity of methylol alkanal described above.

In particular, although the amount of formaldehyde remainder is minimized in a last reactor of the reactor for reducing the amount of formaldehyde remainder, alkyl aldehyde is divisionally added. Accordingly, the amount of alkyl aldehyde is larger than the amount of formaldehyde remainder.

The reactor for reducing the amount of formaldehyde remainder may be driven at the same or higher temperature than that of the reactor for improving selectivity of methylol alkanal within a temperature range of 20 to 80° C. or 50 to 80° C. As a specific embodiment, when the reactor for improving selectivity of methylol alkanal is driven at 50° C., each of the reactors for reducing the amount of formaldehyde remainder (1 to 3 reactors) may be drove at 50° C., or the temperature of at least one reactor thereof may be elevated up to 80° C. and driven.

In another embodiment, when temperature of the reactor for improving selectivity of methylol alkanal is 80° C., all of the reactors for reducing the amount of formaldehyde remainder (1 to 3 reactors) may be driven at 80° C.

This is because the amount of formaldehyde after reaction may be minimized by elevating reaction temperature of the reactor for reducing the amount of formaldehyde remainder than reaction temperature of the reactor for improving selectivity of methylol alkanal. In this regard, when a temperature difference between the two reactors is 30° C. or more, generation of by-products with a high boiling point increases and, thus, a yield of methylol alkanal may be decreased.

In one embodiment, the reactor for improving selectivity of methylol alkanal and the reactor for reducing the amount of formaldehyde remainder, for example, may be independently selected from conventional reactors such as a continuous stirred-tank reactor (CSTR), a Venturi-nozzle reactor, and the like which may control reaction heat.

As described above, in the methylol alkanal prepared according to the present invention, the amount of formaldehyde remainder which acts as a catalyst poison may be reduced by 0.5 to 5.0 wt %, when applied to hydrogenation and, thus, the methylol alkanal may be properly used in preparation of a hydrogenated compound (trimethylolalkane) through hydrogenation.

Advantageous Effects

As apparent from the fore-going, a yield of methylol alkanal may be improved without using formaldehyde in an excess amount of theoretical minimum molar ratio or more according to the present invention, formaldehyde wastewater is reduced, and the amount of formaldehyde remainder, which may act as a catalyst poison in hydrogenation, comprised in methylol alkanal is reduced when prepared methylol alkanal is hydrogenated resulting in improvement of hydrogenation efficiency.

In one embodiment, when normal butylaldehyde was used and a prepared dimethylol butanal was hydrogenated, highly pure trimethylol propane nearly without impurities was prepared.

BEST MODE

Hereinafter, preferred examples will be provided for better understanding of the present invention. It will be apparent to those skilled in the art that these examples are only provided to illustrate the present invention and various modifications and alterations are possible within the scope and technical range of the present invention. Such modifications and alterations fall within the scope of claims included herein.

EXAMPLE 1

Figure 1:
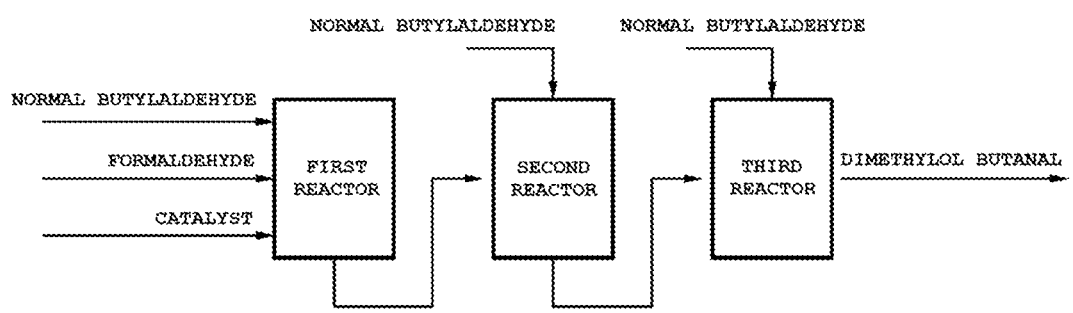
FIG. 1 is a flowchart of a method for preparing dimethylol butanal through a continuous process using a reactor for improving selectivity of methylol alkanal and reactors for reducing the amount of formaldehyde remainder (2 reactors) connected in series, applied to examples of the present invention.

Dimethylolbutanal was prepared using a reaction device illustrated in FIG. 1.

In particular, three 1000 ml continuous stirred-tank reactors (CSTRs) were connected in series. A first reactor thereamong was used as a reactor for improving selectivity of methylol alkanal and the other reactors (hereinafter called second reactor and third reactor for convenience) were used as reactors for reducing the amount of formaldehyde remainder.

First, normal butylaldehyde at a rate of 2.7 g/min, a 42% aqueous formaldehyde solution at a rate of 3.2 g/min, and a triethylamine catalyst at a rate of 0.9 g/min were constantly added to the first reactor. In this regard, a stirrer installed in the first reactor was driven at a rate of 1000 rpm while maintaining a reaction temperature in the reactor at 80° C. to perform reaction.

A reaction product continuously emitted from a lower portion of the first reactor was transferred into the second reactor constituting the reactor for reducing the amount of formaldehyde remainder. Into a pipe for the transfer, fresh normal butylaldehyde was added at a rate of 0.3 g/min such that the fresh normal butylaldehyde was divisionally added into the second reactor. In this regard, a stirrer installed in the reactor was driven at a rate of 1000 rpm while maintaining a reaction temperature within the second reactor at 80° C. to perform reaction.

A reaction product continuously discharged from a lower portion of the second reactor was transferred into the final third reactor constituting the reactor for reducing the amount of formaldehyde remainder. Into a pipe for the transfer, fresh normal butylaldehyde was added at a rate of 0.2 g/min such that the fresh normal butylaldehyde was divisionally added into the third reactor. A stirrer installed in the reactor was driven at a rate of 1000 rpm while maintaining a reaction temperature within the third reactor to 80° C. to perform reaction.

A final reaction product continuously emitted from a lower portion of the third reactor was sampled and each of the amounts of formaldehyde (FA) remainder and the amount of dimethylol butanal were analyzed using gas chromatography. In this regard, a formaldehyde conversion rate and a molar ratio of formaldehyde/normal butylaldehyde were calculated according to calculation methods below. Results are summarized in Table 1 below.

Calculation of formaldehyde(FA)conversion rate: (amount of formaldehyde of raw materials−amount of formaldehyde of reaction product)/amount of formaldehyde of raw materials*100

Calculation of molar ratio of formaldehyde/normal butylaldehyde: (total amount of formaldehyde added to reaction/30)/(total amount of butylaldehyde added to reaction/72.1)

EXAMPLE 2

A process the same as in Example 1 was repeated except that reaction temperatures in the first, second, and third reactors were adjusted as disclosed in Table 1 below and formaldehyde was added to the first reactor at a rate of 1.6 g/min.

EXAMPLE 3

A process the same as in Example 1 was repeated except that reaction temperatures in the first, second, and third reactors were adjusted as disclosed in Table 1 below and formaldehyde was added to the first reactor at a rate of 4.7 g/min.

EXAMPLE 4

A process the same as in Example 1 was repeated except that reaction temperatures in the first, second, and third reactors were adjusted as disclosed in Table 1 below and formaldehyde was added to the first reactor at a rate of 5.1 g/min.

Each of the amount of formaldehyde remainder, the amount of dimethylolbutanol, a formaldehyde conversion rate, and a molar ratio of formaldehyde/normal butylaldehyde was calculated in the same manners as in Example 1. Results are summarized in Table 1 below.

COMPARATIVE EXAMPLE 1

Figure 2:
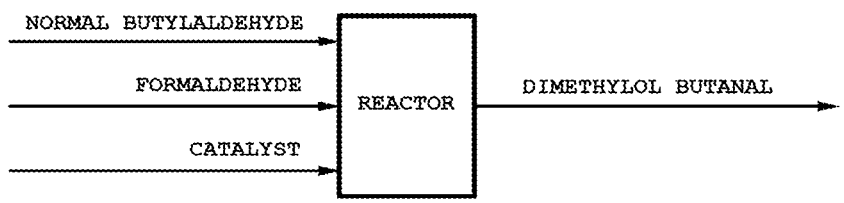
FIG. 2 is a flowchart of a method for preparing dimethylol butanal using a batch reactor applied to conventional technology.

Dimethylolbutanal was prepared using a device illustrated in FIG. 2 instead of FIG. 1.

In particular, normal butylaldehyde at a rate of 1.1 g/min, a 42% aqueous formaldehyde solution at a rate of 1.1 g/min, and a triethylamine catalyst at a rate of 0.3 g/min were continuously added to one 1000 ml continuous stirred-tank reactor (CSTR). In this regard, a stirrer installed in the reactor was driven at a rate of 1000 rpm while maintaining a reaction temperature in the reactor at 80° C. to perform reaction.

Next, each of the amount of formaldehyde (FA) remainder, a formaldehyde (FA) conversion rate, the amount of dimethylol butanal, and a molar ratio of formaldehyde/normal butylaldehyde in a reaction product continuously discharged from a lower portion of the reactor was calculated in the same manner as in Example 1. Results are summarized in Table 1 below.

TABLE 1

| Classification | Amount of FA remainder after reaction wt % | FA conversion rate % | Amount of DMB after reaction wt % | FA/n-BAL mol/mol | Reaction temperature ° C. | No. reactors Types |
|---|---|---|---|---|---|---|
| Example 1 | 1.5 | 92.0 | 30.5 | 1 | 80/80/80 | Three reactors (connected in series) |
| Example 2 | 3.8 | 89.5 | 40.8 | 0.5 | 50/50/50 | Three reactors (connected in series) |
| Example 3 | 0.7 | 93.4 | 26.3 | 1.5 | 80/80/80 | Three reactors (connected in series) |
| Example 4 | 3.9 | 80.0 | 42 | 1.63 | 50/80/80 | Three reactors (connected in series) |
| Comparative Example 1 | 5.5 | 50.3 | 7.1 | 1.5 | 80 | One reactor |

As shown in Table 1, it can be confirmed that, in Examples 1 to 4 according to the present invention, dimethylol butanal comprising 0.7 to 3.9 wt % of the formaldehyde remainder after reaction may be prepared, a reaction molar ratio of the formaldehyde to the normal butylaldehyde is 0.5 to 1.63, and the amount of dimethylol butanal is 26.3 to 42%.

On the other hand, it can be confirmed that, in Comparative Example 1 according to conventional technology, dimethylol butanal comprising 5.5 wt % of the formaldehyde remainder is prepared after reaction, a reaction molar ratio of the formaldehyde to the normal butylaldehyde is 1.5, and the amount of dimethylol butanal is 7.1%.

Furthermore, in Examples 1 to 4 according to the present invention, a ratio of the amount of methylol alkanal (%) to the amount of formaldehyde remainder (%) was calculated as 10 or more, particularly 10.736 to 37.571, a ratio of the amount of methylol alkanal (%) to the formaldehyde conversion rate (%) calculated from the amount of formaldehyde remainder was calculated as 0.25 or more, particularly 0.281 to 0.525. On the other hand, in Comparative Example 1, a ratio of the amount of methylol alkanal (%) to the amount of formaldehyde remainder (%) was calculated as 1.5 or less, particularly 1.29, and a ratio of the amount of methylol alkanal (%) to the formaldehyde conversion rate (%) calculated from the amount of formaldehyde remainder was calculated as 0.15 or less, particularly 0.141.

What is claimed is:

1. A method of preparing methylol alkanal through a reaction of formaldehyde and alkyl aldehyde in the presence of an amine based catalyst,
    wherein the methylol alkanal comprises 0.5 to 5 wt % of a formaldehyde remainder of a total of reaction product,
    wherein the reaction is carried out using a continuous reaction device comprising 2 to 4 reactors in which the reactors are connected in series, and
    wherein the alkyl aldehyde is divisionally added to the 2 to 4 reactors.

2. The method according to claim 1, wherein a reaction molar ratio of the formaldehyde to the alkyl aldehyde is 2 or less.

3. The method according to claim 1, wherein an amount of the added formaldehyde is 20 to 70 wt % with respect to 100 wt % of alkyl aldehyde.

4. The method according to claim 1, wherein, a ratio of an amount of the methylol alkanal (%) to an amount of the formaldehyde remainder (%) in the reaction product of the methylol alkanal is 10 or more.

5. The method according to claim 1, wherein, in the methylol alkanal, a ratio of an amount of the methylol alkanal (%) to a formaldehyde conversion rate (%) calculated from an amount of the formaldehyde remainder is 0.25 or more.

6. The method according to claim 1, wherein the the 2 to 4 reactors comprises a first equipped reactor for improving selectivity of the methylol alkanal and a reactor for reducing an amount of the formaldehyde remaining in the methylol alkanal, which are connected in series.

7. The method according to claim 6, wherein alkyl aldehyde is divisionally added to the reactor for improving selectivity of the methylol alkanal and the reactor for reducing the amount of formaldehyde remainder.

8. The method according to claim 6, wherein formaldehyde and tertiary amine are added batchwise to the reactor for improving selectivity of the methylol alkanal.

9. The method according to claim 6, wherein the reactor for reducing the amount of formaldehyde remainder is constituted of 1 to 3 reactors.

10. The method according to claim 6, wherein the reactor for reducing the amount of formaldehyde remainder is driven at temperature the same as or higher than that of the reactor for improving selectivity of the methylol alkanal within a range of 20 to 80° C.

11. The method according to claim 6, wherein the reactor for improving selectivity of the methylol alkanal and the reactor for reducing the amount of formaldehyde remainder are independently selected from a continuous stirred-tank reactor and a Venturi nozzle reactor.

12. The method according to claim 1, wherein the methylol alkanal is applied to hydrogenation.

13. The method according to claim 7, wherein the reactor for reducing the amount of formaldehyde remainder is constituted of 1 to 3 reactors.

14. The method according to claim 7, wherein the reactor for reducing the amount of formaldehyde remainder is driven at temperature the same as or higher than that of the reactor for improving selectivity of the methylol alkanal within a range of 20 to 80° C.

15. The method according to claim 7, wherein the reactor for improving selectivity of the methylol alkanal and the reactor for reducing the amount of formaldehyde remainder are independently selected from a continuous stirred-tank reactor and a Venturi nozzle reactor.

* * * * *